(12) United States Patent
Bailey, III et al.

(10) Patent No.: US 7,025,901 B2
(45) Date of Patent: Apr. 11, 2006

(54) ALKYL AND ARYL TRIFLUOROMETHOXYTETRAFLUOROSULFURANES

(75) Inventors: Wade H. Bailey, III, Emmaus, PA (US); Reno Joseph Pesaresi, Jr., Easton, PA (US); William Jack Casteel, Jr., Emmaus, PA (US); Guido Peter Pez, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 224 days.

(21) Appl. No.: 10/620,237

(22) Filed: Jul. 15, 2003

(65) Prior Publication Data

US 2005/0012072 A1    Jan. 20, 2005

(51) Int. Cl.
*C09K 19/06*   (2006.01)
*C01B 3/04*    (2006.01)
*C07C 69/76*   (2006.01)
*C07C 317/00*  (2006.01)

(52) U.S. Cl. .................. 252/299.6; 549/374; 560/109; 568/27

(58) Field of Classification Search .................... None
See application file for complete search history.

(56) References Cited

U.S. PATENT DOCUMENTS 5,055,223 A    10/1991    Reiffenrath et al. .... 252/299.62

FOREIGN PATENT DOCUMENTS

| DE | 10008505 | 2/2000 |
|---|---|---|
| DE | 10018086 | 4/2000 |
| WO | 8810251 | 12/1988 |

OTHER PUBLICATIONS

T. Inoi, "Fluorinated Liquid Crystals," Organofluorine Chemistry, Ch. 12, 1994, pp. 263-286.
P. Kirsch, et al, "Nematic Liquid Crystals for Active . . . ," Angew, Chem. Int. Ed., 2000, 39, pp. 4216-4235.
P. Kirsch, et al, "Liquid Crystals Based on . . . ," Angew, Chem. Int. Ed. 1999, 38, pp. 1989-1992.
G. Pass, et al, "Some Reactions of Pentafluorosulfur . . . ," Inorg. Chem. 2, 1963, pp. 1016-1019.
T. Kitazume, et al, "Some Chemistry of Fluorinated . . . ," J. Am. Chem. Soc., 100, 1978, pp. 492-496.
D. B. Denny, et al, J. Am. Chem. Soc., 95, 1973, pp. 8191-8192.
X. Ou, et al, "Oxidative Addition and Isomerization . . . ," Can. J. Chem., 75, 1997, pp. 1878-1884.

(Continued)

*Primary Examiner*—Paul A. Zucker
(74) *Attorney, Agent, or Firm*—Geoffrey L. Chase

(57) ABSTRACT

Novel compositions containing $SF_4$—O—$CF_3$ bonded to an organic group are disclosed. Aryl trifluoromethoxytetrafluorosulfuranes (or Ar—$SF_4$—O—$CF_3$), have been synthesized via the reaction of an aryl disulfide or thiol with fluoroxytrifluoromethane ($F_3COF$). The compositions are useful synthons, which may be derivatized to yield highly electrically polar molecules, particularly novel liquid crystal compositions having high dielectric anisotropies. Cycloalkyl trifluoromethoxytetrafluorosulfuranes have similar utility.

11 Claims, 1 Drawing Sheet

OTHER PUBLICATIONS

D.P. Curran, "Fluorous Reverse Phase . . . ," Synlett, 9, 2001, pp. 1488-1496.

M. Brenner, et al, "Gas Phase Molecular . . . ," Advanced Materials, 5, 1993, pp. 842-848.

LiqCryst: LC 1262 and LiqCryst: LC 4394; Liquid Crystal Group: Hamburg, Germany.

D.R. Lide, "Handbook of Chemistry and Physics", Sec. 9, 1995, pp. 9-50.

W.A. Sheppard, "The Electrical Effect of the Sulfur . . . ," J. Am. Chem. Soc., 84, 1962, pp. 3072-3076.

W.A. Sheppard, "Arylsulfur Pentafluorides," J. Am. Chem. Soc., 84, 1962, pp. 3064-3072.

W.A. Sheppard, "The Effect of Fluorine Substitution . . . ," J. Am. Chem. Soc., 85, 1963, pp. 1314-1318.

fac-cismer-trans-

ALKYL AND ARYL TRIFLUOROMETHOXYTETRAFLUOROSULFURANES

BACKGROUND OF THE INVENTION

The present invention pertains to new compositions of matter, particularly aryl trifluoromethoxytetrafluorosulfuranes, which may be derivatized to yield highly electrically polar molecules, particularly novel liquid crystal compositions having high dielectric anisotropies.

Liquid crystals are an essential component of many types of optical displays. The usefulness of liquid crystals for application in this area is related to the strength and position of the polar groups in the liquid crystal molecule and the degree of dielectric anisotropy the liquid crystal exhibits (1). Accordingly, the literature shows that a number of liquid crystals used in active matrix displays have evolved into those containing highly polar head groups (1,2), quite notably perfluorinated ones such as $CF_3$, which impart a dipole on the molecule in order to achieve an improved dielectric anisotropy and hence enhanced performance.

Early research showed that the introduction of additional lateral fluorine atoms would augment the molecular dipole moment, and therefore increase the dielectric anisotropy and enhance performance. However, this process of lateral fluorination had a negative effect on other properties of the product, such as clearing points of the liquid crystals. Therefore, research began to focus on identification of new, highly polar terminal groups, which induce reasonably high clearing points while still increasing the dielectric anisotropy (2).

The search for new liquid crystal head groups is ongoing, as evident from the application of the highly polar —$SF_5$ group in the synthesis of nematic liquid crystals (3,4). While an evaluation of physical properties demonstrated that —$SF_5$-based liquid crystals were a polar class of liquid crystals compatible with active matrix display technology, several less favorable properties also became evident. First, the experimentally determined dielectric anisotropies of the newly synthesized —$SF_5$ derivatives were far lower that predicted. Additionally, the liquid crystals had a relatively high rotational viscosity, as well as a relatively high melting point (3).

The chemical moiety, —$SF_4$—$OCF_3$, has been reported in the literature as a component of a handful of inorganic compositions including those best characterized such as $F_5SOCF_3$ (5) and the cis- and trans- isomers of $F_4S(OCF_3)_2$ (6). A recent patent (7) suggests liquid crystal compositions containing the —$CF_2$—$SF_4$—$OCF_3$ group linked to various organic structures; however, no such compositions were synthesized or explicitly described (see also (7a)). In particular, there is no prior art or actual compound where the $SF_4$—$OCF_3$ group is attached to an organic moiety. Although reactions between aryl sulfides and $F_3COF$ (fluoroxytrifluoromethane) have been reported (8), the investigators did not disclose any products containing S—O—$CF_3$ bonded centers. Otherwise, the use of —$SF_4$—$OCF_3$ as a functional group has remained unexplored.

Accordingly, it is desired to provide liquid crystal compositions having high dielectric anisotropies, which do not substantially suffer from the aforementioned deficiencies of other liquid crystal compositions.

All references cited herein are incorporated herein by reference in their entireties.

BRIEF SUMMARY OF THE INVENTION

Accordingly, the invention provides a composition comprising $RSF_4OCF_3$, wherein R is an organic group and $SF_4OCF_3$ is bonded to a carbon of the organic group.

Further provided is a composition comprising $RSF_4OCF_3$, wherein R comprises a ring of six carbon atoms.

Preferably, R is substituted or unsubstituted cyclohexyl and more preferably R is substituted or unsubstituted phenyl or naphthyl.

Also provided is a composition comprising a structure of the following formula:

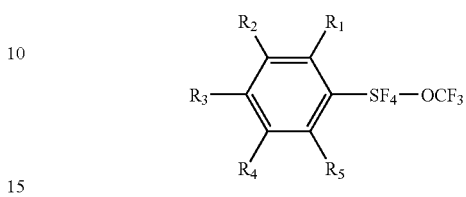

wherein $R_1$, $R_2$, $R_3$, $R_4$, and $R_5$ are members independently selected from the group consisting of H, alkyl, aryl, cycloalkyl, halogen, nitro, perfluoroalkyl, cyano, methoxy, trifluoromethoxy, sulfur pentafluoride and (trifluoromethoxy)tetrafluorosulfuranyl.

The invention further provides an aryl trifluoromethoxytetrafluorosulfarane.

Still further provided is a composition comprising a structure of the following formula:

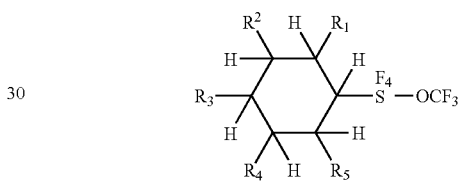

wherein $R_1$, $R_2$, $R_3$, $R_4$, and $R_5$ are members independently selected from the group consisting of H, alkyl, aryl, cycloalkyl, halogen, nitro, perfluoroalkyl, cyano, methoxy, trifluoromethoxy, sulfur pentafluoride and (trifluoromethoxy)tetrafluorosulfuranyl.

Still further provided is a process for preparing a composition of the invention, said process being represented by the following equation:

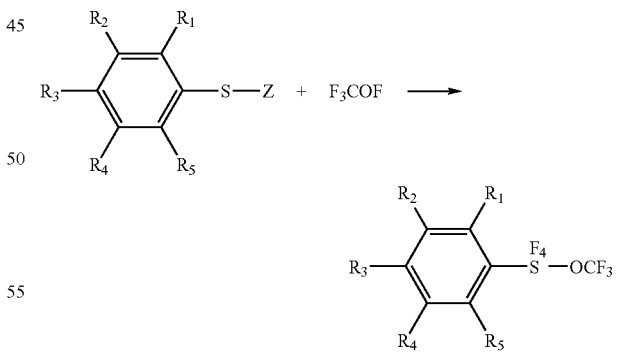

where S-Z is S—H, disulfide (i.e., S—S wherein the sulfurs are bonded to identical Ar groups to form a dimer joined by a disulfide bond: Ar—S—S—Ar), S—Cl or $SF_3$.

Still further provided is a process for preparing a composition of the invention, said process comprising reacting an aryl sulfurchlorotetrafluoride or an aryl sulfurbromotetrafluoride with a source of —$OCF_3$, such that the —$OCF_3$ displaces a chlorine atom from the aryl sulfurchlorotetrafluoride or a bromine atom from the aryl sulfurbromotetrafluoride by direct combination, photo-catalytic reaction, or thermally induced displacement, to provide the composition.

Still further provided is a process for preparing a composition of the invention, said process comprising reacting an arylsulfur trifluoride with an active fluoride base and an oxidative source of —$OCF_3$ to provide the composition.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

The present invention looks to solve the problem of attaining a high dielectric anisotropy without a significant negative effect on other properties. This invention proposes the unique functional group, —$SF_4$—$OCF_3$, bonded to an organic structure as a new composition of matter. The compositions are useful synthons, which may be derivatized to yield highly electrically polar molecules, particularly novel liquid crystal compositions having high dielectric anisotropies. The new compositions of matter have been synthesized via the reaction of an aryl disulfide or thiol with fluoroxytri-fluoromethane.

Certain embodiments of the invention described herein comprise a new composition of matter represented by the formula R—$SF_4$—$OCF_3$, wherein R is an organic group. The nature of the organic group is not particularly limited, provided that a carbon of the organic group is bonded to the sulfur of $SF_4OCF_3$. Non-limiting examples of suitable organic groups include alkyl, cycloalkyl, polycycloalkyl, substituted aryl, substituted naphthyl, polyolefin compounds where —$SF_4OCF_3$ substitutes for hydrogen in the polymer chain, polystyrenes where —$SF_4OCF_3$ is a substituent on the aromatic ring, oxygen-containing heterocycles, nitrogen-containing heterocycles, sulfur-containing heterocycles, compounds with non-aromatic unsaturation such as acetylenes and olefins, or other —$SF_4OCF_3$ containing organic compounds made by analogy to known —$CF_3$ and —$SF_5$— containing organics (see, e.g., refs. 17 and 18).

Preferred embodiments of the invention comprise a new composition of matter represented by the general structure:

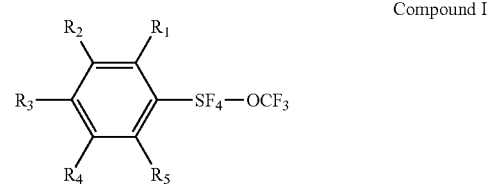

Compound I in which $R_1$, $R_2$, $R_3$, $R_4$, and $R_5$ may consist of groups that generally include but are not limited to H, alkyl, aryl, cycloalkyl, halogen, nitro, perfluoroalkyl, cyano, methoxy, trifluoromethoxy, sulfur pentafluoride, additional (trifluoromethoxy)tetrafluorosulfuranyl (—$SF_4OCF_3$) groups, and other groups that are relatively inert to the conditions used for making the new composition (or if reactive, can be substituted for relatively inert protecting groups present during synthesis) and that may prove useful in themselves or for conversion to or attachment of other valuable functional groups.

Figure 1:
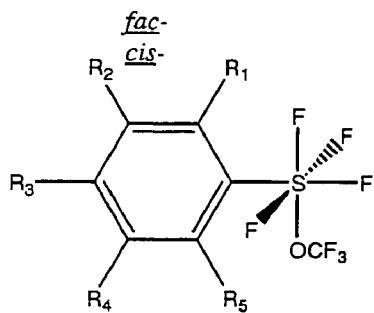
FIG. 1 is a chemical structure of an aryl trifluoromethoxytetrafluoro-sulfurane of the invention in which the —$SF_4OCF_3$ moiety exists as a fac- (or cis-) isomer.
Figure 2:
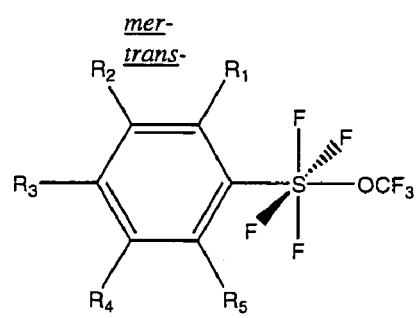
FIG. 2 is a chemical structure of an aryl trifluoromethoxytetrafluoro-sulfurane of the invention in which the —$SF_4OCF_3$ moiety exists as a mer- (or trans-) isomer.

As shown in FIGS. 1 and 2, the —$SF_4OCF_3$ moiety exists as two isomers, fac- (or cis-) and mer- (or trans-). These isomers are generally stable and do not readily isomerize at room temperature.

Compound I may, in principle, be chemically derivatized using conventional techniques to form other novel compositions that may include liquid crystalline materials that are useful as components of liquid crystal electronic displays. The nature of suitable "tail groups" added to Compound I is not particularly limited, provided that the resulting compound has desirable properties, e.g., acceptable properties for use either alone or as a component of liquid crystal mixtures. In certain embodiments of the invention, each of $R_1$, $R_2$, $R_4$, and $R_5$ are as defined above (e.g., H) and $R_3$ is represented by one of the following formulas:

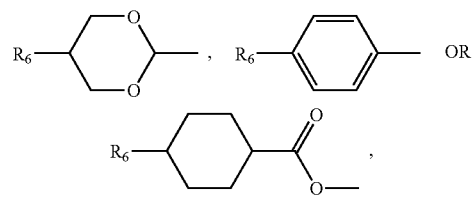

wherein $R_6$ is a alkyl, cycloalkyl or substituted phenyl. In certain embodiments, alkyl is $C_1$ to $C_{18}$ alkyl.

For example, Compound I can be derivatized to provide compounds having the general structures of Compounds II, III, and IV, shown below:

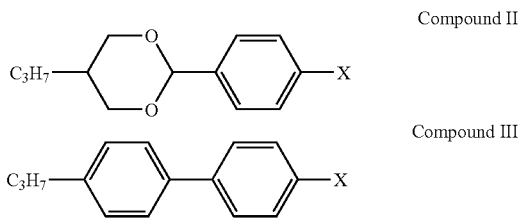

Compound II

Compound III

-continued

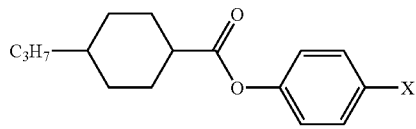

Compound IV

Where, for example, X represents —$CF_3$, —CN, —$SF_5$, or —$OCF_3$, the compounds are known and exhibit properties that render them useful as liquid crystals or in mixtures thereof for application in electronic displays. Here, the "head group", —X, performs the critical function of providing a molecule with a strong dipole moment. This moment, $\mu$, and the electrical polarizability anisotropy, $\Delta\alpha$, of the molecule are fundamental properties that determine the efficacy or utility of the molecule as a component in liquid crystal displays and are highly dependent on the nature of the head group, —X, and the organic structure to which it is attached.

In order to illustrate the utility of compounds of the present invention for the design and synthesis of new liquid crystal compositions, we have predicted by established methods of calculation the performance of the exemplary Compounds II, III, and IV where —X is —$SF_4OCF_3$ and compared these properties to those of the likewise calculated and experimentally determined properties for the aforementioned known compositions (i.e., Compounds II, III, and IV where X is —$CF_3$, —CN, —$SF_5$, or —$OCF_3$).

Our quantum mechanical based computational method consisted of first generating a structure using Spartan Version 5.1.3 (Schrodinger, LLC) and performing using this software package an initial geometry optimization with the semi-empirical Parametric Method 3 methodology. The resulting structure was optimized further using Density Functional Theory B3LYP/6–31 G* computational method of the Jaguar Version 4.1 (Schrodinger, LLC) software package; it has been previously demonstrated (3) that hexavalent sulfur fluorides require such ab initio or Density Functional Theory methods for a reliable prediction of their dipole moments. The comparative calculated dipoles, $\mu$, and polarizability anisotropies, $\Delta\alpha$ (Equation 1), $$\text{Equation 1: } \Delta\alpha = \alpha_{zz} - \sqrt{\frac{\alpha_{yy}^2 + \alpha_{xx}^2}{2}}$$

$\Delta\alpha$=Polarizability anisotropy
$\alpha_{zz}$=Polarizability of molecular long axis
$\alpha_{yy}$=Polarizability of first molecular short axis
$\alpha_{xx}$=Polarizability of second molecular short axis of different compositions (Tables 1 and 2) were then calculated using the single point, ab initio HF/6–31 G* methodology with coupled-perturbed Hartree-Fock polarization from the optimized structure.

Figure 3:
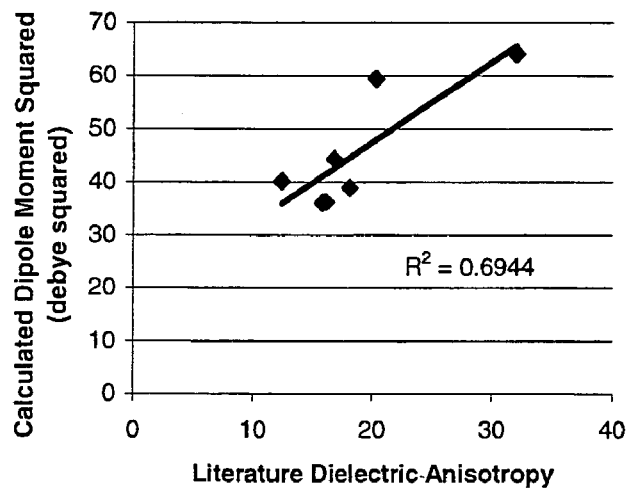
FIG. 3 is a plot of the calculated square of the dipole moment ($\mu^2$) against published dielectric anisotropy ($\Delta\epsilon$) values for several prior art liquid crystal compositions.
Figure 4:
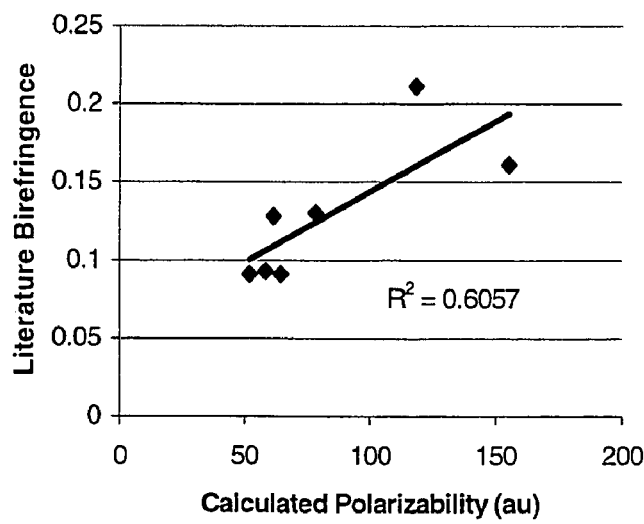
FIG. 4 is a plot of the published optical birefringence ($\Delta\epsilon$) values against the calculated polarizability anisotropy ($\Delta\alpha$) for several prior art liquid crystal compositions.

Desired parameters for engineering a liquid crystal display are its dielectric anisotropy, $\Delta\epsilon$, and optical birefringence, $\Delta\eta$. It has been shown in the literature (11) that $\Delta\epsilon$ is approximately proportional to the square of the dipole moment, $\mu^2$, and that $\Delta\eta$ is approximately proportional to the polarizability anisotropy, $\Delta\alpha$. The correlation between these quantities for the previously known Compounds II, III, and IV are demonstrated in FIGS. 3 and 4. From the thus statistically derived relationships between $\Delta\epsilon$ and $\mu^2$ as well as $\Delta\eta$ and $\Delta\alpha$, values for $\Delta\epsilon$ and $\Delta\eta$ were estimated for Compounds II to IV wherein —X is —$SF_4OCF_3$ and are displayed in parentheses in Table 1.

It is evident from these results that structures II to IV where X is —$SF_4OCF_3$, which can be derived from the Compound I, have $\Delta\epsilon$ and $\Delta\eta$ values that are consistent with those of known liquid crystals. Furthermore, the calculated dipole values and corresponding dielectric anisotropies of these —$SF_4OCF_3$ compounds approach or exceed those of the comparative high-performing cyano-substituted models especially for the mer-isomer, thus, indicating promising potential for liquid crystals constructed with Compound I as the molecules' leading group that contain the —$SF_4OCF_3$ "head".

TABLE 1

Calculation and Comparison of Liquid Crystal Physical and Optical Properties.

| Compound | Total $\mu_{calc.}$ (in debye) | $\Delta\alpha_{calc.}$ (in au) | $\Delta\epsilon_{lit.}$ (estimated) | $\Delta\eta_{lit.}$ (estimated) |
|---|---|---|---|---|
| II-CN | 8.01 | 78.2 | 32[12] | 0.13[12] |
| II-$CF_3$ | 6.02 | 58.3 | 16.1[2] | 0.093[2] |
| II-$SF_5$ | 7.71 | 64.3 | 20.3[3] | 0.091[3] |
| II-$OCF_3$ | 5.52 | 60.8 | — | — |
| II-fac-$SF_4OCF_3$ | 7.79 | 59.8 | — (28.7) | — (0.107) |
| II-mer-$SF_4OCF_3$ | 8.37 | 63.1 | — (34.9) | — (0.110) |
| III-CN | 6.24 | 118.4 | 18.1[12] | 0.211[12] |
| III-$CF_3$ | 4.01 | 88.4 | — | — |
| III-$SF_5$ | 6.01 | 155.2 | 15.8[3] | 0.161[3] |
| III-$OCF_3$ | 3.45 | 87.9 | — | — |
| III-fac-$SF_4OCF_3$ | 5.92 | 103.2 | — (11.8) | — (0.146) |
| III-mer-$SF_4OCF_3$ | 6.38 | 103.2 | — (15.5) | — (0.146) |
| IV-CN | 6.66 | 61.4 | 16.8[11] | 0.128[11] |
| IV-$CF_3$ | 4.82 | 53.6 | — | — |
| IV-$SF_5$ | 6.34 | 51.9 | 12.4[3] | 0.091[3] |
| IV-$OCF_3$ | 4.55 | 63.5 | — | — |
| IV-fac-$SF_4OCF_3$ | 6.58 | 101.1 | — (17.2) | — (0.144) |
| IV-mer-$SF_4OCF_3$ | 6.84 | 74.5 | — (19.5) | — (0.121) |

Note:
Superscripted numbers in parentheses refer to literature reference numbers.

Thus, in certain embodiments, the invention comprises a liquid crystal containing a (trifluoromethoxy)tetrafluorosulfuranyl group as a head group, wherein the composition has a dielectric anisotropy ($\Delta\epsilon$) of at least 11 (preferably at least 15, more preferably at least 19, even more preferably at least 34) and an optical birefringence ($\Delta\eta$) of at least 0.1 (preferably at least 0.11, more preferably at least 0.12, even more preferably at least 0.14).

A lateral fluorination of the liquid crystal molecule and/or the incorporation of select linking groups for tuning of physical properties have also been well established (1,2) and should offer good possibilities for preparing —$SF_4OCF_3$ containing molecules with desirable anisotropic properties. Comparative calculated and literature data demonstrating the dipole-enhancing effect of lateral fluorination on the exemplary Compounds V, VI, and VII are displayed in Table 2.

TABLE 2

Total calculated dipole moment for lateral-fluorinated groups in debye.

Compound V

Y = CN, $CF_3$, $OCF_3$,
$SF_5$, fac-$SF_4OCF_3$,
and mer-$SF_4OCF_3$

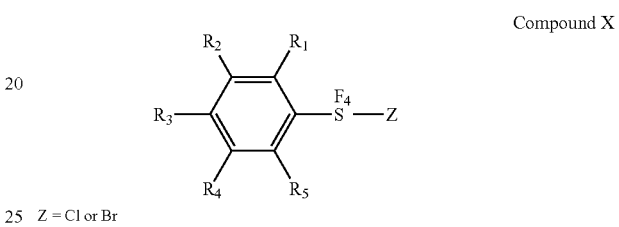

Compound VI

Compound VII

| Head Group-Y | Compound V | Compound VI | Compound VII |
|---|---|---|---|
| —OCF$_3$ | 2.79 (2.36)[16] | 3.72 | 4.12 |
| —CF$_3$ | 3.09 (2.86)[13] | 4.13 | 4.56 |
| —SF$_5$ | 4.63 (3.44)[14] | 5.28 | 5.67 |
| —CN | 4.94 (4.18)[13] | 5.84 | 6.37 |
| -fac-SF$_4$OCF$_3$ | 4.95 | 5.32 | 5.75 |
| -mer-SF$_4$OCF$_3$ | 5.27 | 5.77 | 6.31 |

Note:
Literature values are given in parentheses with the corresponding reference number in superscript.

It should also be feasible to hydrogenate Compound I to produce the cyclohexyl analog, Compound VIII, which may also be employed in similar fashion to its aromatic counterpart as a synthon for highly polar head groups.

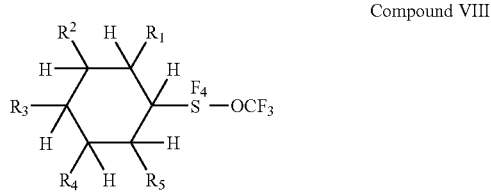

Compound VIII

The preferred process for synthesizing Compound I is shown in the following equation (i.e., Reaction 1):

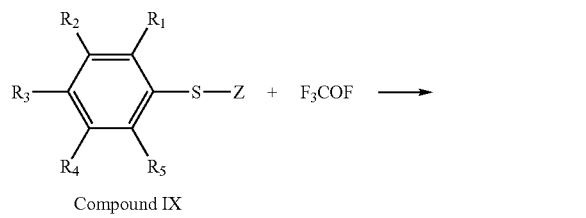

Compound IX

Compound I in which —Z can be —H, a second sulfide group (i.e., wherein Compound IX is a dimer of two monomers joined by a disulfide bond: Ar—S—S—Ar), —Cl, or where S—X represents the intermediate —SF$_3$ (15) group. Reaction 1 may be performed at temperatures ranging from 0° C. to 120° C. but more preferably between 20° C. and 80° C. and is dependent upon the reactivity of the substrate, Compound IX. The reaction may be performed with neat compound 1× or in the presence of an inert solvent that may be selected from but is not limited to classes of solvents such as nitriles (acetonitrile), freons (CFC-113), perfluorocarbons (FC-72), halocarbons (chloroform), alkanes (decane), deactivated arenes (1,3-bis(trifluoromethyl) benzene), non-oxidizing acids (anhydrous HF), or mixtures thereof. The fluorinating agent, fluoroxytrifluoromethane (CF$_3$° F.), may be added to the reactor in batch quantities or in a continuous stream in concentrations ranging from 1% to 100% with a balance of N$_2$, O$_2$, air, F$_2$, CO, CO$_2$, Ar, He, F$_2$CO, SF$_6$ or any combination of these; concentrations between 5% and 20% CF$_3$° F. are preferred.

Reaction 1 is not the only means for synthesizing Compound I. Another approach is to first generate the previously reported aryl sulfurhalidetetrafluoride (9), or Compound X:

Compound X

Z = Cl or Br then react it with a source of —OCF$_3$ such as CF$_3$OF, F$_3$COCl, F$_3$COOCF$_3$, or a variety of known F$_3$CO$^-$ salts to affect the displacement of the chlorine or bromine atom by direct combination, photo-catalytic reaction, or a thermally induced displacement. Another potential synthesis is by treatment of the corresponding arylsulfur trifluoride intermediate with an active fluoride base (i.e. anhydrous tetramethylammonium fluoride) and an oxidative CF$_3$O— source such as F$_3$COOCF$_3$.

The fac- and mer- isomers of ArSF$_4$OCF$_3$ can be separated via chromato-graphic means. Preparative, fluorous reverse phase HPLC (10) is the preferred chromatographic method since it provides an excellent resolution of the isomers. Ideally, a fractional distillation should allow the facile separation of the isomers.

The invention will be illustrated in more detail with reference to the following Examples, but it should be understood that the present invention is not deemed to be limited thereto.

EXAMPLES

Experimental Background

4-Bromobenzene thiol (Acros) was used to make 4-bromophenyl disulfide as described herein. Anhydrous acetonitrile (Acros) was used without further purification. Reactors consisted of ¾" or 1" FEP tubes heat-sealed at one end and capped with a T316 S.S. compression fitting; the compression fitting contained two ports attached to T316 S.S. valves serving as inlets; the reactor inlet ran to the bottom of the reactor via ¼" FEP tubing to a 10 μm filter as a gas sparger. The solvent and compound IX were charged to the reactors under nitrogen and the reactors were sealed. The reactors were attached to a flow manifold that supplied a stream of 8% CF$_3$OF at ambient pressure and allowed the analysis of the reactor effluent by FTIR (ProspectIR, MIDAC) in order to follow the reaction progress. An FEP U-trap immersed in ice followed the reactor to trap condensable materials that may have escaped at elevated temperatures. NMR spectra were obtained using a Bruker 500 MHz FTNMR spectrometer. GC-MS were obtained using an HP-5890IIGC/HP7972 MSD combination. Preparative HPLC was performed using an HP-1100 Series HPLC fitted with a 200 μL sample loop servicing a 250 nm X 10 mm Fluophase PFP (5 μm particle, 100 A pore) semi-preparative column with guard cartridge and was followed at 254 nm using a high pressure UV cell.

Example 1

4-Bromophenyl Disulfide

4-Bromobenzene thiol (25.0 g, 132 mmol) and methanol (250 mL, Fisher Scientific) were added to a 500 mL round bottom flask containing a Teflon coated stir bar. Excess elemental iodine (36 g, 140 mmol) was added in 2 g portions directly to the rapidly stirred thiol solution, precipitating the disulfide. The reaction was complete when the dark color of iodine persisted. The reaction mixture was added to 250 mL of water, which was then carefully neutralized with solid sodium bicarbonate then with sodium bisulfite, to neutralize any remaining $I_2$. The resulting slurry was then extracted three times with 50 mL of methylene chloride; the organic layers were combined, dried over magnesium sulfate, and filtered. Removal of the solvent on a rotary evaporator revealed a light yellow solid, crude 4-bromophenyl disulfide (24.5 g, 98.7%). The disulfide was recrystallized from boiling methanol then fused under vacuum to remove any remaining solvent.

Example 2

4-Bromophenyl (trifluoromethoxy) tetrafluorosulfurane

4-Bromophenyl disulfide (5 g, 13 mmol) was charged to an FEP tube reactor with acetonitrile (15 mL). At a total flow rate of 200 mL/min, a mixture of 8% $CF_3OF$ in nitrogen was passed through the reactor contents at 25° C. until a total of 72 mmol (ca.) $CF_3OF$ had been added. FTIR analysis of the effluent during the reaction indicated that not all of the $CF_3OF$ had been consumed. While continuously adding $CF_3OF$, the reactor was externally heated to 75° C. At this temperature, all of the solvent had been carried away in the effluent leaving only the substrate, a yellow liquid. After a total of about 300 mmol of $CF_3OF$ had been passed through the reactor, the reactor was cooled to 20° C. The reactor contents were dissolved in pentane and neutralized with aqueous sodium bicarbonate. The aqueous layer was extracted 3 times with 10 mL portions of pentane and the organic layer was concentrated on a rotary evaporator revealing the crude product as a yellow oil (3.25 g). Analysis of the crude product by GC-MS indicated a 12% presence, by relative peak area, of the 4-bromophenyl (trifluoromethoxy) tetrafluorosulfurane isomers in a 1:1 ratio (fac-4-bromophenyl (trifluoromethoxy) tetrafluorosulfurane, GC-MS m/z (% relative intensity, ion): 350 (100, M+2), 348 (100, M+), 265/263 (48, M—$OCF_3$), 242/240 (83, M—$SF_4$), 176/174 (35, M—$SF_4$ & $F_2CO$), 157/155 (91, M—$SF_4OCF_3$), 95 (78, M—$SF_4$ & Br), 69 (84, $CF_3$)); (mer-4(trifluoromethoxy) tetrasulfurane, GC-MS m/z (% relative intensity, ion): 350 (52, M+2), 348 (52, M+), 265/263 (27, M—$OCF_3$), 176/174 (100, M—$SF_4$ & $F_2CO$), 157/155(30, M —$SF_4OCF_3$), 95 (98, M—$SF_4$ & Br), 69 (66, $CF_3$)). 4-bromophenyl sulfurpentafluorid and ring fluorinated versions of these products constituted the majority of the observed byproducts. $^{19}$F-NMR of the product mixture in $CD_3CN$ indicated a similar product distribution (fac-4-bromophenyl (trifluoromethoxy) tetrafluorosulfurane, $^{19}$F-NMR ($CD_3CN$, δ): +93.5 (dtq, 1F, J=149.6, 149.6, 18.6 Hz), +67.8 (dtq, 1F, J=149.6, 149.6, 6.0 Hz), +66.7 (ddq, 2F, J=149.6, 149.6, 15.6 Hz), −55.4 (m, 3F)); (mer-4-bromophenyl (trifluoromethoxy) tetrafluorosulfurane, $^{19}$F NMR ($CD_3CN$, δ): +74.6 (q, 4F, J=10.0 Hz), −56.3 (pent, 3F, J=10.0 Hz)). The isomers were isolated using semi-preparative, fluorous reverse phase HPLC[10]; small aliquots of the crude product were separated using the isocratic mixture of 65% methanol and 35% water at a flow of 5 mL/min. NMR and GC-MS data for the pure materials coincided with those assigned in the crude mixture. The reaction was repeated replacing 4-bromophenyl disulfide with 4-bromobenzene thiol, producing similar results.

The present invention provides new compositions of matter that can act as a building block for other highly polar molecules, and more specifically, liquid crystals. The apparently high dipole moment of these new compounds can potentially give rise to high dielectric anisotropies for liquid crystal compositions containing these compounds.

While the invention has been described in detail and with reference to specific examples thereof, it will be apparent to one skilled in the art that various changes and modifications can be made therein without departing from the spirit and scope thereof.

The invention claimed is:

1. A composition comprising $RSF_4OCF_3$, wherein R is an organic group selected from the group consisting of a substitutied or unsubstituted cyclohexyl, a substituted or unsubstituted phenyl or napthyl and mixtures thereof and $SF_4OCF_3$ is bonded to a carbon of the organic group.

2. A composition comprising a structure of the following

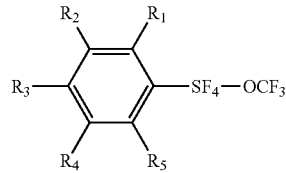

formula:
wherein $R_1$, $R_2$, $R_3$, $R_4$, and $R_5$ are members independently selected from the group consisting of H, alkyl, aryl, cycloalkyl, halogen, nitro, perfluoroalkyl, cyano, methoxy, trifluoromethoxy, sulfur pentafluoride and (trifluoromethoxy)tetrafluorosulfuranyl, or wherein each of $R_1$, $R_2$, $R_4$, and $R_5$ is H and $R_3$ is represented by one of the following formulas:

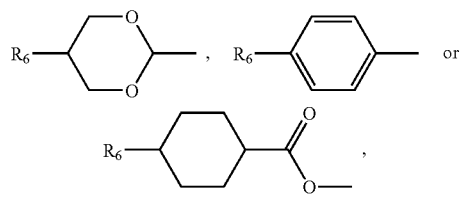

wherein $R_6$ is a alkyl, cycloalkyl or substituted phenyl.

3. The composition of claim 2, wherein the composition is a liquid crystal and a (trifluoromethoxy)tetrafluorosulfuranyl group of the structure is a head group of the liquid crystal having a dielectric anisotropy of at least 11 and an optical birefringence of at least 0.1.

4. The composition of claim 2, wherein the $SF_4OCF_3$ is present in the composition solely in a fac form.

5. The composition of claim 2, wherein the $SF_4OCF_3$ is present in the composition solely in a mer form.

6. The composition of claim 2, wherein at least one of $R_1$ and $R_5$ is F.

7. A composition comprising a structure of the following formula:

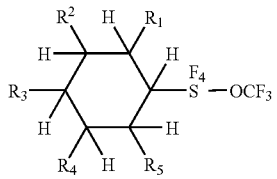

wherein $R_1$, $R_2$, $R_3$, $R_4$, and $R_5$ are members independently selected from the group consisting of H, alkyl, aryl, cycloalkyl, halogen, nitro, perfluoroalkyl, cyano, methoxy, trifluoromethoxy, sulfur pentafluoride and (trifluoromethoxy)tetrafluorosulfuranyl, or wherein each of $R_1$, $R_2$, $R_4$, and $R_5$ is H and $R_3$ is represented by one of the following formulas:

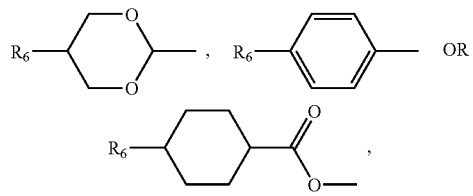

wherein $R_6$ is a alkyl, cvcloalkyl or substituted phenyl.

8. The composition of claim 7, wherein the composition is a liquid crystal and a (trifluoromethoxy)tetrafluorosulfuranyl group of the structure is a head group of the liquid crystal having a dielectric anisotropy of at least 11 and an optical birefringence of at least 0.1.

9. The composition of claim 7, wherein the $SF_4OCF_3$ is present in the composition solely in a fac form.

10. The composition of claim 7, wherein the $SF_4OCF_3$ is present in the composition solely in a mer form.

11. The composition of claim 7, wherein at least one of $R_1$ and $R_5$ is F.

* * * * *